United States Patent
Cha et al.

(10) Patent No.: US 6,634,242 B2
(45) Date of Patent: Oct. 21, 2003

(54) APPARATUS FOR MEASURING RESPIRATORY GAS FLOW BY MEANS OF A DISPOSABLE RESPIRATORY TUBE

(76) Inventors: Un Jong Cha, 208-205 Jugong 2 Apt., Mochung-dong, Heungdeok-gu, Cheongju-city, Chungcheongbuk-do (KR); Kyoung A Kim, 1207, Deokhee Apt., Sajik 2-dong, Heungdeok-gu, Cheongju-city, Chungcheongbuk-do (KR); Hyun Sik Kim, 604-1101, Kukhwa-hansin Apt., Samcheon-dong, Seo-Gu, Daejeon Metropolitan-City (KR)

( * ) Notice: Subject to any disclaimer, the term of this patent is extended or adjusted under 35 U.S.C. 154(b) by 0 days.

(21) Appl. No.: 10/123,115
(22) Filed: Apr. 17, 2002

(65) Prior Publication Data
US 2003/0101827 A1 Jun. 5, 2003

(30) Foreign Application Priority Data
Dec. 5, 2001 (KR) .......................... 2001-76675

(51) Int. Cl.[7] ............................... G01F 1/46
(52) U.S. Cl. ................... 73/861.66; 73/861.65
(58) Field of Search ................ 73/861.66, 861.65

(56) References Cited
U.S. PATENT DOCUMENTS 4,559,836 A * 12/1985 Coleman et al. ......... 73/861.66
4,735,100 A * 4/1988 Hajto ..................... 73/861.66
5,817,950 A * 10/1998 Wiklund et al. ......... 73/861.66
6,044,716 A * 4/2000 Yamamoto .............. 73/861.66

* cited by examiner

Primary Examiner—Hezron Williams
Assistant Examiner—Takisha S Miller
(74) Attorney, Agent, or Firm—Birch, Stewart, Kolasch & Birch, LLP (57) ABSTRACT

Disclosed is an apparatus for measuring respiratory gas flow, which provides a high accuracy in measurement of the respiratory gas flow and reduces the manufacturing cost of the apparatus, in comparison with the conventional disposable apparatus for measuring respiratory gas. The apparatus includes a measurement module and a respiratory tube assembly. The respiratory tube assembly comprise a cylindrical tube body and a sensing rod inserted through the cylindrical tube body. The sensing rod is shaped like the number "1" and has a plurality of sampling pores and two air passages. Locations of the sampling pores are determined by equal area division method in which a circular section of the cylindrical tube body is divided into a plurality of annuluses with equal areas and the sampling pores are formed at the positions also equally dividing the annuluses to which the sampling pores belong.

4 Claims, 6 Drawing Sheets

APPARATUS FOR MEASURING RESPIRATORY GAS FLOW BY MEANS OF A DISPOSABLE RESPIRATORY TUBE

This nonprovisional application claims priority under 35 U.S.C. § 119(a) on Patent Application No. 2001-76675 filed in Korea on Dec. 5, 2001, which is herein incorporated by reference.

BACKGROUND OF THE INVENTION

1. Field of the invention

The present invention relates to an apparatus for measuring respiratory gas flow by utilizing dynamic pressure, and more particularly to an apparatus for measuring respiratory gas flow, which includes a disposable respiratory tube assembly assembled with a measurement module, so as to not only improve the accuracy in the measurement of the respiratory gas flow but also reduce the manufacturing cost of the apparatus.

2. Description of the Prior Art

In an examination of vital capacity, which is a clinical examination or clinical practice, change in the capacity of a human lung during respiration is continuously recorded and analyzed, so as to estimate and present all intermediary parameters, thereby assisting in diagnosing respiratory impairments.

As an apparatus for measuring respiratory gas flow which has been most widely used up to now, generally known to the public, are apparatuses of pneumotach type, in which a resistive element is disposed in the middle of a respiratory tube, and pressure difference between both sides of the resistive element is measured, thereby evaluating a flow quantity of the respiratory gas.

In order to measure the respiratory gas flow by means of such an apparatus of pneumotach type, employed is a relational expression between the flow quantity and the static pressure, which is the Rohrer's equation, a quadratic function expressed as the following equation 1.

$$\Delta P = R_0 * F + R_1 * F^2 \qquad \text{Equation 1}$$

In equation 1, $\Delta P$ is a pressure difference, $R_0$ and $R_1$ are constants, and F is a flow quantity of respiratory gas.

As apparent from equation 1, when the apparatus of pneumotach type is utilized in measuring the respiratory gas flow, two constants $R_0$ and $R_1$ should be determined, thereby not only complicating the measuring process but also inevitably increasing errors of the measurement at least by two times in comparison with measurement of the respiratory gas flow, which employs a single constant. That is, the measurement of the respiratory gas flow by means of the pneumotach type apparatus could have bad linearity and incorrect null adjustment, thereby deteriorating the measurement accuracy.

In order to overcome such problems as described above, U.S. Pat. No. 5,060,655, issued to Rudolph, discloses a pneumotach apparatus for measuring gas flows, which employs a respiratory tube having resistive elements to the respiratory gas flow in the respiratory tube, so that $R_1$ in equation 1 is zero.

However, in the Rudolph's pneumotach apparatus, the resistive elements have very complicated construction and their manufacturing cost is expensive, so that it is difficult to manufacture and sell a respiratory tube having the resistive elements as a disposable apparatus. Therefore, the respiratory tube must be used permanently or repeatedly, thereby causing severe sanitary problems.

Further, in such apparatuses of pneumotach type, the resistive elements are located in the middle of the path of an examined person's respiratory gas, so as to disturb the examined person's respiration and thereby change a flow signal which represents the examined person's respiratory performance, thereby deteriorating the reliability of the examination for the respiratory performance.

In the meantime, U.S. Pat. No. 5,038,773, issued to Norlien, et al., discloses a respiratory gas flow measuring system, which measures the respiratory gas flow by measuring dynamic pressure instead of the static pressure, so as to overcome the above-mentioned problems.

Figure 7:
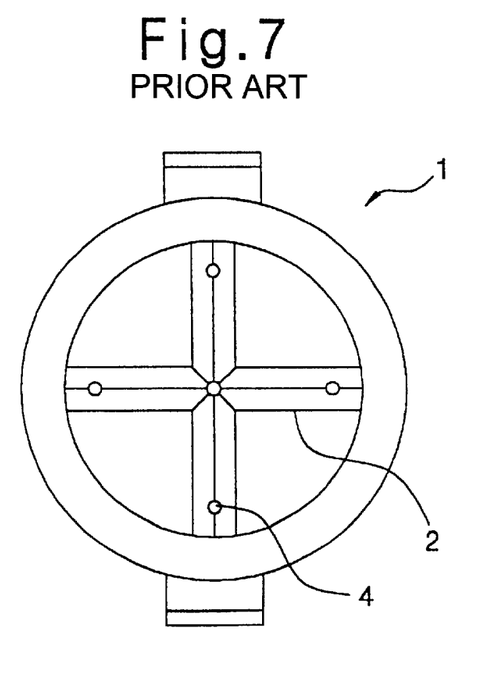
FIG. 7 is a left side view of a cylindrical respiratory tube employed in the previously invented respiratory gas flow measuring system.
Figure 8:
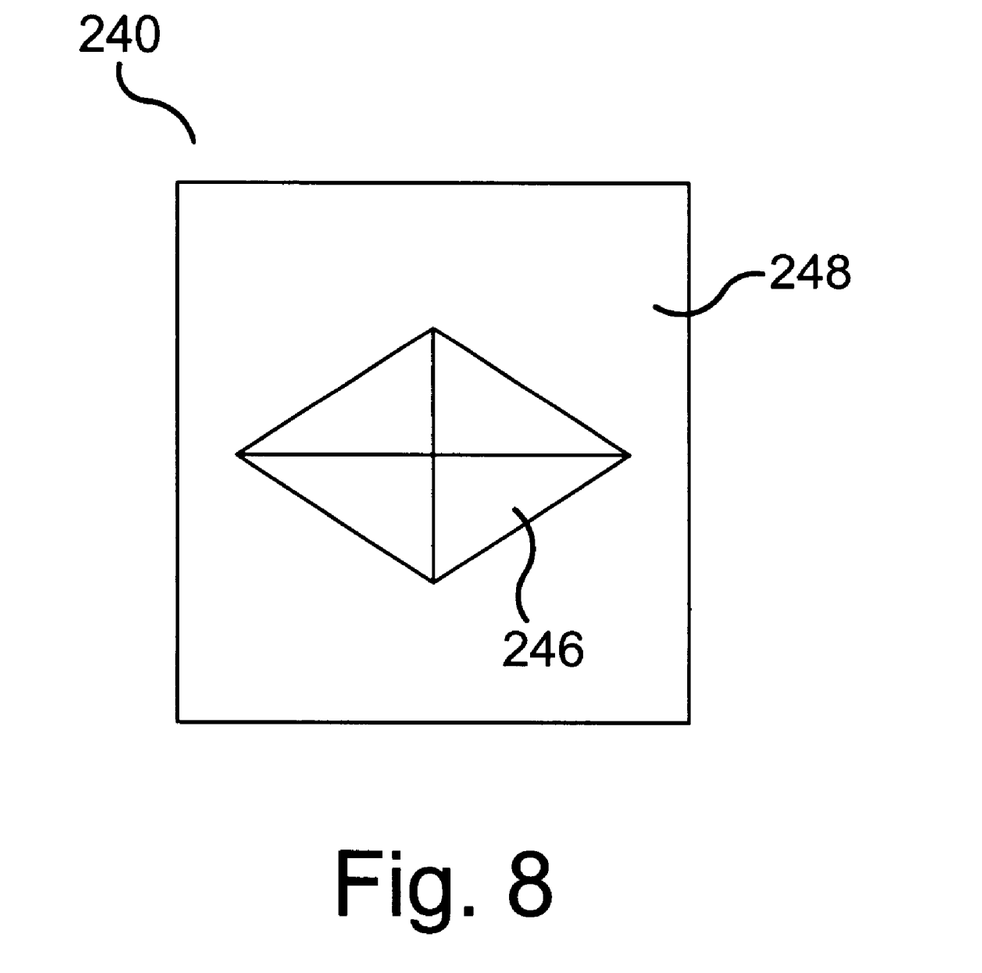
FIG. 8 is a top view of the sensing rod of FIG. 3.

FIG. 7 is a left side view of a cylindrical respiratory tube or a tubular barrel, which is employed in the Norlien's respiratory gas flow measuring system.

As shown in FIG. 7, the conventional respiratory tube 1 contains a pair of ribs 2, which intersect at their midpoints to form a cross and centrally disposed relative to a midpoint of the respiratory tube 1. Fine apertures 4 for sampling the flow of the respiratory gas are formed near distal ends of the ribs 2 and at the center of the respiratory tube 1 at which the ribs intersect. The fine apertures 4 are symmetrically arranged, so as to the respiratory gas flow in both directions.

When the respiratory gas flow is measured by the respiratory gas flow measuring system as described above, the following relational expression, equation 2, is established between the respiratory gas flow and the dynamic pressure of the respiratory gas, provided that the respiratory gas flow has a constant velocity in the radial direction of the cylindrical respiratory tube.

$$F = A*u = A*\sqrt{\frac{2}{\rho}}*\sqrt{P_D} \propto \sqrt{P_D} = S*\sqrt{P_D} \qquad \text{Equation 2}$$

In equation 2, A is a sectional area of the cylindrical respiratory tube, S is a proportional factor, $P_D$ is the dynamic pressure, u is velocity of the respiratory gas, and $\rho$ is density of the respiratory gas.

Equation 2 shows that the quantity of the respiratory gas flow is proportional in principle to the square root of the dynamic pressure and there exits only one proportional factor S in equation 2. Therefore, it can be understood that the measurement errors are reduced and the null adjustment is more simplified in the respiratory gas flow measuring system, in comparison with the apparatus of pneumotach type.

The Norlien's respiratory gas flow measuring system as described above has considerably overcome the existing problems such as the disturbance of respiration by the resistive elements and the complicated construction of the resistive elements.

However, in the Norlien's respiratory gas flow measuring system as described above, the respiratory gas flow is sampled only at four location near a cylindrical wall of and at the center of the tubular barrel, but is not sampled between the center and the cylindrical wall of the tubular barrel, so that the measurement error of the respiratory gas flow is inevitably large.

Further, in the Norlien's respiratory gas flow measuring system, the respiratory tube, or the tubular barrel, is made from plastic and has a complicated construction, thereby increasing the manufacturing cost, so that the Norlien's respiratory gas flow measuring system has a low economical efficiency when it is used as a disposable apparatus.

SUMMARY OF THE INVENTION

Accordingly, the present invention has been made to solve the above-mentioned problems occurring in the prior art, and it is an object of the present invention to provide an apparatus for measuring respiratory gas flow, which provides a high accuracy in measurement of the respiratory gas flow and reduces the manufacturing cost of the apparatus, in comparison with the conventional disposable apparatus for measuring respiratory gas.

In order to accomplish this object, there is provided an apparatus for measuring respiratory gas flow, the apparatus comprising: a measurement module containing a differential pressure sensor and a thermistor; and a respiratory tube assembly detachably assembled with the measurement module, wherein the respiratory tube comprises: a cylindrical tube body having two rod holes formed through a cylindrical wall of the cylindrical tube body, the rod holes being disposed at opposite ends of a diameter of the cylindrical tube body, each of the rod holes having a shape of a diamond; and a sensing rod detachably inserted through the rod holes, the sensing rod having an appearance of a number "1", the sensing rod having a cross-section shaped like a diamond, the sensing rod having a plurality of sampling pores and two air passages formed vertically through the sensing rod, the air passages being separated from each other, the sampling pores being formed through both sides of a sensing rod body of the sensing rod, first half of the sampling pores facing toward an entrance of the respiratory tube assembly and communicating with a first one of the air passages, second half of the sampling pores facing toward an exit of the respiratory tube assembly and communicating with a second one of the air passages, the first half of the sampling pores being located symmetrically to the second half of the sampling pores, wherein locations of the sampling pores are determined by an equal area division method in which a semi-circular section of the cylindrical tube body is divided into a plurality of annuluses with equal areas and the sampling pores are formed at the positions also equally dividing the areas of the annuluses which the pores belong to.

It is preferred that the sensing rod comprises the sensing rod body, a pyramidal head formed on the sensing rod body, and a base formed under the sensing rod body, which are integrated with each other, the pyramidal head having a lower surface whose area is larger than a sectional area of the sensing rod body, so as to form an upper jaw between the sensing rod body and the pyramidal head, the base having a sectional area larger than the sectional area of the sensing rod body, so as to form a lower jaw between the base and the sensing rod body, the upper jaw and the lower jaw enabling the sensing rod to be stably fixed in the respiratory tube assembly.

BRIEF DESCRIPTION OF THE DRAWINGS

The above and other objects, features and advantages of the present invention will be more apparent from the following detailed description taken in conjunction with the accompanying drawings, in which.

DETAILED DESCRIPTION OF THE PREFERRED EMBODIMENTS

Hereinafter, a preferred embodiment of the present invention will be described with reference to the accompanying drawings.

Figure 1:
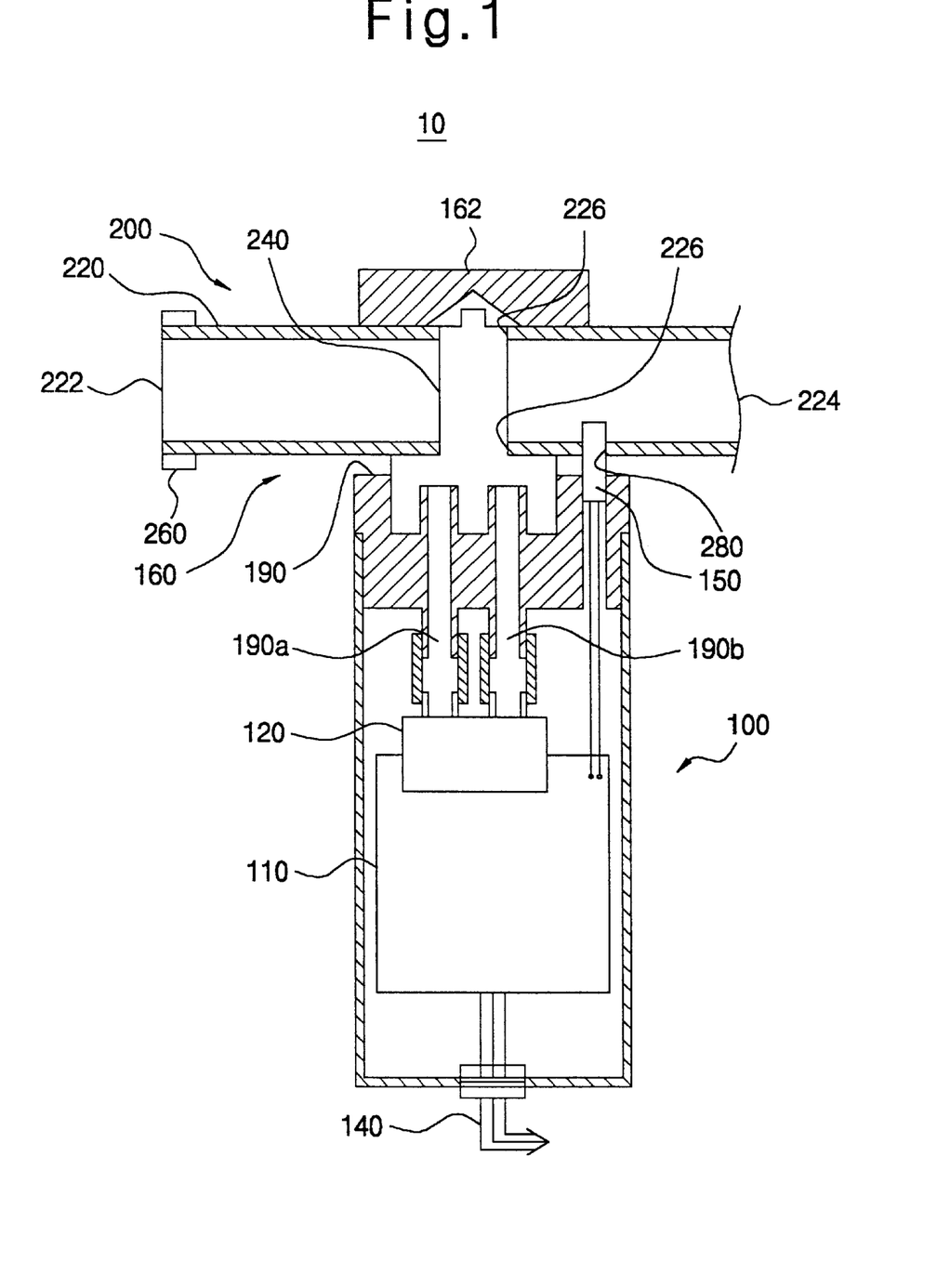
FIG. 1 is a longitudinal sectional view of an apparatus for measuring respiratory gas flow according to the present invention.

As shown in FIG. 1, an apparatus 10 for measuring respiratory gas flow according to the present invention includes a measurement module 100 having a grip shape and a respiratory tube assembly 200 detachably assembled with the measurement module 100.

Also, according to present embodiment, the apparatus 10 for measuring respiratory gas flow may further include a stand (not shown) for placing the measurement module 100 when the measurement module 100 is stored or not used.

The measurement module 100 includes a printed circuit board 110, a differential pressure sensor 120 attached to the printed circuit board 110, and an electronic circuit (not shown). The differential pressure sensor 120 detects dynamic pressure applied to a sensing rod 240 of the respiratory tube assembly 200 which will be described later. The dynamic pressure detected by the differential pressure sensor 120 is converted into an electric voltage signal, and then is subjected to analog/digital conversion, by the electronic circuit. Thereafter, the converted signal is sent through a connection lead 140 to a main examination system of respiratory gas flow, such as a computer.

Further, the measurement module 100 may further comprise a thermistor 150 so as to measure temperature of the respiratory gas passing through the respiratory tube assembly 200. In this case, one end of the thermistor 150 is installed in the measurement module 100 while the other end of the thermistor 150 is fitted in a thermistor hole 280 formed through the respiratory tube assembly 200.

Moreover, the measurement module 100 has an assembly hole 160 formed between a pivotal canopy 162 and an upper end of the measurement module 100. The pivotal canopy 162 is pivotally installed on an upper end of the measurement module 100. When the respiratory tube assembly 200 is assembled with the measurement module 100, the respiratory tube assembly 200 with the sensing rod 240 is put on the upper end of the measurement module 100 in a state where the pivotal canopy 162 is open, and then the pivotal canopy 162 is pivoted to clamp the respiratory tube assembly 200, so that the respiratory tube assembly 200 is firmly fitted in the assembly hole 160 of the measurement module 100. In this way, the respiratory tube assembly 200 can be easily assembled with the measurement module 100. In other words, the pivotal canopy 162 enables the respiratory tube assembly 200 to be easily assembled with and separated from the measurement module 100.

Referring to FIG. 1, the respiratory tube assembly 200 includes a cylindrical tube body 220 made from paper, and a sensing rod 240 detachably inserted in the cylindrical tube body 220.

Figure 2:
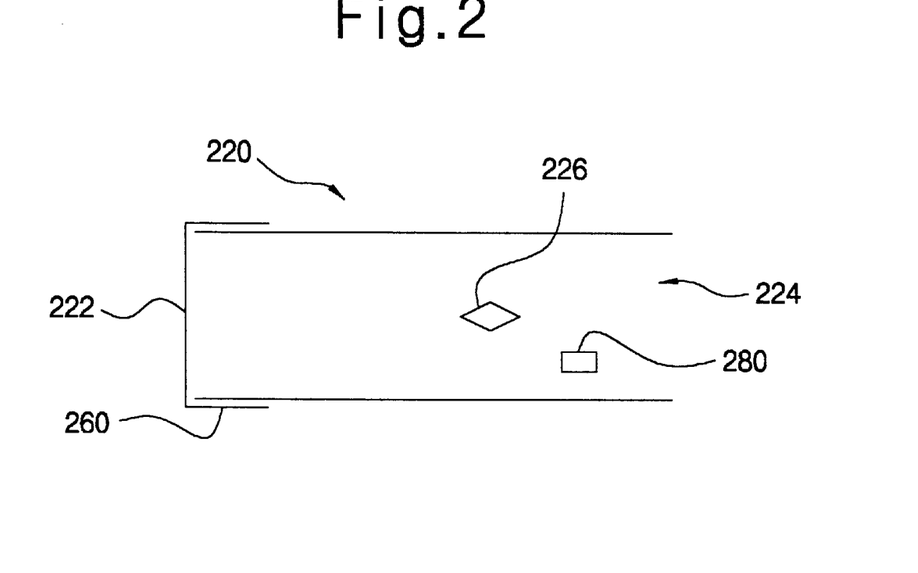
FIG. 2 is a schematic partial side view of the apparatus shown in FIG. 1.

As shown in FIG. 2, the cylindrical tube body 220 has an entrance 222 and an exit 224, and a screen cap 260 having a net shape is capped on the entrance 222 so as to stabilize streamline of the respiratory gas.

Moreover, two rod holes 226 having a diamond shape are formed through a cylindrical wall of the cylindrical tube body 220. When the respiratory tube assembly 200 is assembled with the measurement module 100, one of the rod holes 226 is located at the uppermost position of the respiratory tube assembly 200 and the other of the rod holes 226 is located at the lowermost position of the respiratory tube assembly 200. Further, it is preferred that the thermistor hole 280 in which the thermistor 150 is inserted is formed through the cylindrical wall of the cylindrical tube body 220.

Hereinafter, the sensing rod 240, which samples the respiratory gas flow in the respiratory tube assembly 200 and transforms it into the dynamic pressure, will be described.

Figure 3:
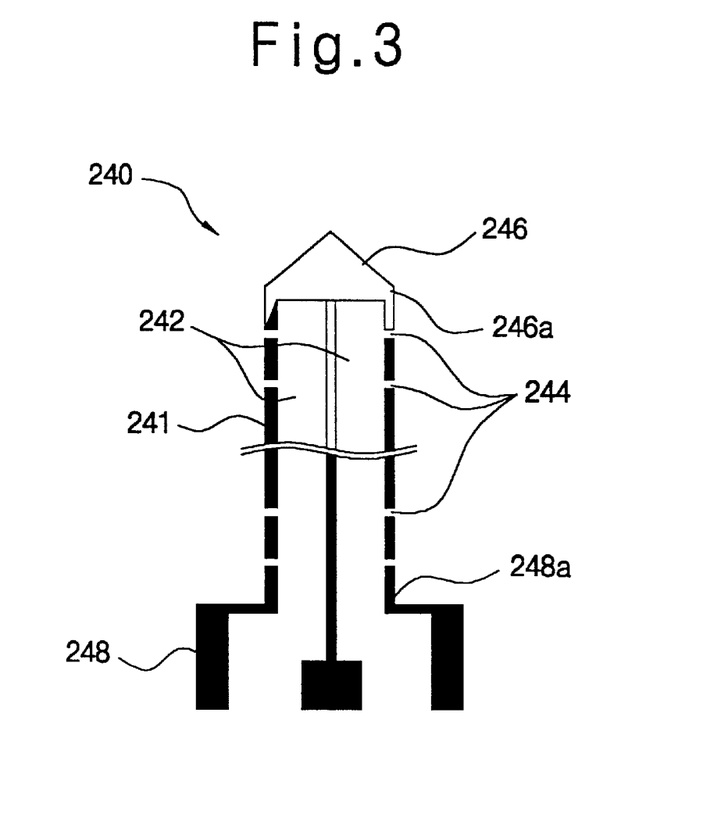
FIG. 3 is a schematic sectional view of a sensing rod employed in the apparatus shown in FIG. 1.
Figure 4:
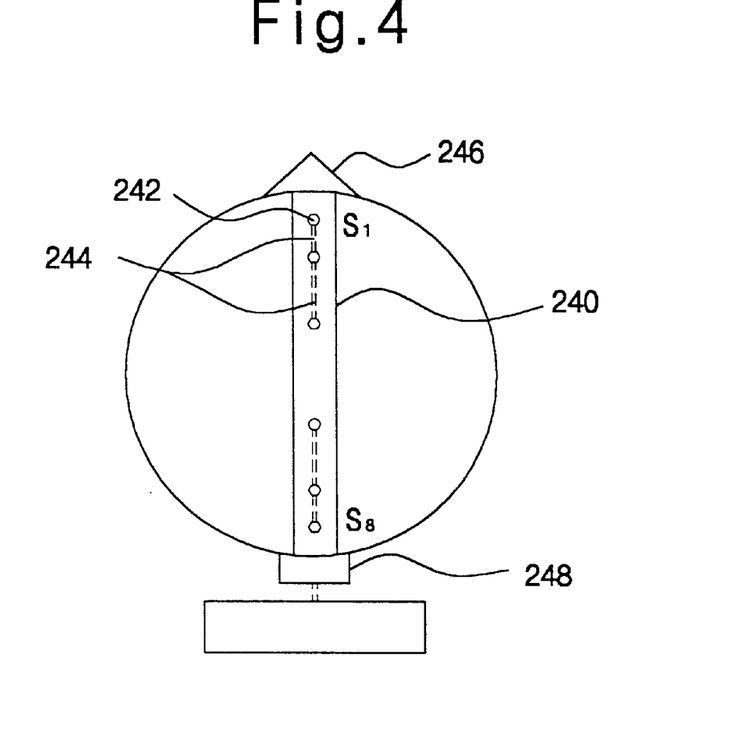
FIG. 4 is a transverse sectional view of an apparatus for measuring respiratory gas flow according to the present invention, in which a respiratory tube assembly is assembled with a measurement module, the respiratory tube assembly having a plurality of sampling pores whose locations are determined by an equal area division method.

As shown in FIGS. 3 and 4, the sensing rod 240 has a shape of the number "1" and is completely inserted through the rod holes 226 formed through the cylindrical wall of the cylindrical tube body 220.

Further, the sensing rod 240 has a section of a diamond shape so as to stabilize the streamline of the respiratory gas.

As shown best in FIG. 3, the sensing rod 240 has a plurality of sampling pores 244, and two air passages 242 connected perpendicularly to the sampling pores 244, thereby communicating with the differential pressure sensor 120 in the measurement module 100. In this case, the sampling pores 244 are symmetrically formed toward the entrance 222 and the exit 224 of the respiratory tube assembly 200, so as to sample the respiratory gas flow in both directions through the sensing rod 240.

When the velocity of the respiratory gas is measured in order to measure the respiratory gas flow, positions of the sampling pores 244 on the sensing rod 240 have a large influence on the measurement of the respiratory gas flow. It is because the velocity of the respiratory gas is different according to a position in the cylindrical tube body 220. In general, in a cylindrical tube in which gas passes, the velocity of the gas is the largest at the center of a circular cross-section of the cylindrical tube, decreases as a location of measuring the velocity goes radially outward from the center of the cross section, and becomes zero at the surface of the wall of the cylindrical tube, that is, at the circumference of the circular cross section.

Therefore, in order to generally measure the velocity of the respiratory gas between the center and the wall of the cylindrical tube body, the sensing rod 240 has a shape of the number "1" and has a plurality of the sampling pores 244 arranged symmetrically in the vertical direction along the sensing rod 240.

Especially, it is preferred that the locations of the sampling pores 244 formed through the sensing rod 240 are determined by an equal area division method which will be described in detail hereinafter.

The present invention proposes a method of dividing the sectional area of the cylindrical tube body into portions with the same area, thereby optimally sampling the velocity of the respiratory gas flow, in order to reduce the measurement error of the respiratory gas flow as much as possible.

When the velocity of the gas at a location spaced a radius r from the center of the cylindrical tube body is defined as u(r), the following integral equation, that is, equation 2, is established between the quantity F and the velocity u(r) of respiratory gas flow.

$$F = \int u(r)dA(r) = 2\pi \int r \cdot u(r) dr \qquad \text{Equation 3}$$

As apparent from FIG. 3, the quantity F of the respiratory gas flow could be estimated with a knowledge of change of the velocity u according to the radius r, that is, with a knowledge of distribution of the velocity at a random position in the circular cross-section. However, in a general human respiratory gas, the velocity of its flow is not constant, and the velocity cannot be expressed by a single function with respect to all the radius r. Therefore, the velocity must be measured with respect to all the radius r.

However, it is impossible to measure the velocity with respect to all the radius r. Accordingly, there is no alternative except that a finite number of representative points are selected in the circular cross-section of the cylindrical tube body and the velocity of the respiratory gas flow is measured at the selected points. In order to obtain the respiratory gas flow by means of a finite number of velocity samples, an equation of weighted sum, equation 4 as follows, is employed instead of the integral expression, equation 3.

$$\hat{F} = 2\pi \sum_{k=1}^{N} r_k \cdot u(r_k) \qquad \text{Equation 4}$$

In equation 4, k is the number of velocity samples, and N is the total number of the velocity samples.

In this case, $\hat{F}$ is an estimated value of the respiratory gas flow which is estimated from the velocity samples. When the number of the velocity samples goes to infinity, equation 4 converges to the integral expression, equation 3. However, since the number of the velocity samples is actually finite, there inevitably exits an error in the estimation of the respiratory gas flow from the velocity of the respiratory gas.

Figure 5A:
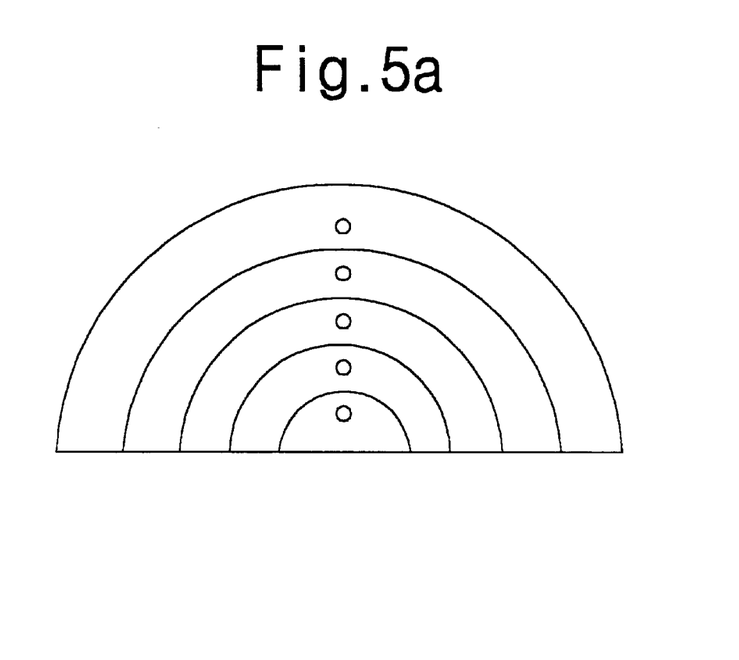
FIGS. 5a to 5c are views showing three methods of determining locations for sampling the respiratory gas flow.
Figure 5B:
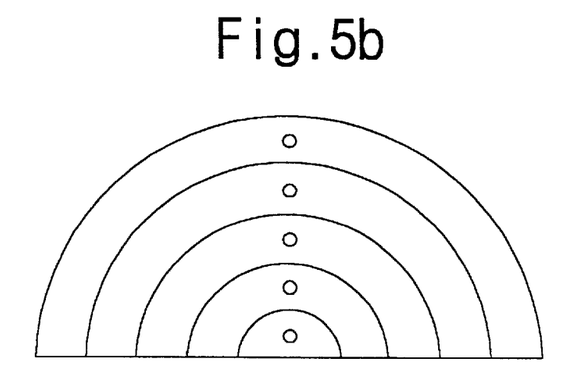
Figure 5C:
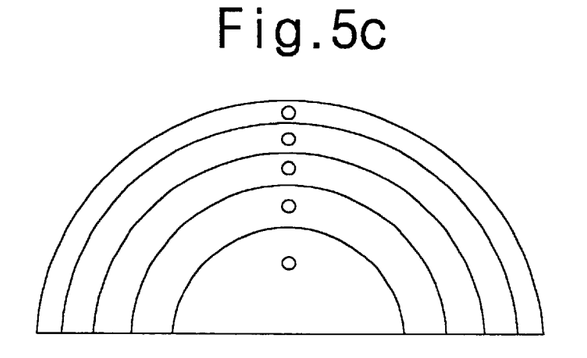

FIGS. 5a to 5c show three ways of determining the representative locations at which the velocity of the respiratory gas is sampled.

Only the upper semi-circular section is considered in FIGS. 5a to 5c, since the velocity of the respiratory gas is presumably the same at locations spaced the same distance from the center of the cylindrical tube body.

FIG. 5a shows an equal interval division method in which the locations for sampling the respiratory gas velocity are arranged at the same intervals between the center (r=0) and the wall (r=1), FIG. 5b shows an equal radius division method in which the semi-circular section is divided into a plurality of annuluses with the same radial widths and the locations for sampling the respiratory gas velocity are arranged at middle positions of the annuluses, and FIG. 5c shows an equal area division method in which the semi-circular section is divided into a plurality of annuluses with the same areas and the locations for sampling the respiratory gas velocity are arranged at the positions also equally dividing the annuluses which the sampling locations belong to.

The gas flow is estimated by multiplying the flow velocity by the sectional area, and the flow velocity at a specific representative location in the cylindrical tube body reflects the flow velocity only in a certain area adjacent to the representative location. In consideration of this fact, when the location for sampling the respiratory gas velocity is determined by the equal area division method as described above, the velocity gradient in the cylindrical tube body can be reflected best and the sampling error can be reduced, thereby heightening the accuracy in the measurement of the respiratory gas flow.

Hereinafter, described will be a mathematical comparison of measurement errors in the case where the locations for sampling the respiratory gas velocity are determined by the three methods as described above, that is, the equal interval division method, the equal radius division method, and the equal area division, method.

The following relational expression, equation 5, may be established between the radius r of the cylindrical tube body and the velocity of the respiratory gas.

$$u(r)=1-r^m \quad \text{Equation 5}$$

In equation 5, m is an exponent, or a degree, and is generally larger than two, and it is assumed that the radius of the cylindrical tube body is one and the maximum velocity of the flow through the center of the cylindrical tube body is one regardless of the exponent m. However, the generality in a derivation of the equation is maintained. In this case, a true value of the respiratory gas flow can be obtained by putting equation 5 into equation 3.

$$F = \frac{m}{2(m+2)} \quad \text{Equation 6}$$

In this case, N number of the representative locations $r_k$ for sampling the respiratory gas flow are obtained by the equation 4 and 5 resulting in the following expressions according to the above-mentioned three division methods.

In the case of the equal interval division method:

$$r_k = \frac{k}{N+1} \quad \text{Equation 7}$$

In the case of the equal radius division method:

$$r_k = \frac{2k-1}{2N} \quad \text{Equation 8}$$

In the case of the equal area division method:

$$r_k = \sqrt{\frac{2k-1}{2N}} \quad \text{Equation 9}$$

In the above three equations, k=1, 2, ..., N.

Thereafter, the velocities $u_k$ of the respiratory gas are obtained by inserting the representative locations into equation 5, and then the respiratory gas flow is obtained as follows by inserting the locations and the velocities into equation 4.

In the case of the equal interval division method:

$$\hat{F} = \frac{1}{8(N+1)^2}\left[9u_1 + 3(4N+1)u_N + 8\sum_{k=2}^{N-1} k \cdot u_k\right] \quad \text{Equation 10}$$

In the case of the equal radius division method:

$$\hat{F} = \frac{1}{2N^2}\sum_{k=1}^{N}(2k-1)u_k \quad \text{Equation 11}$$

In the case of the equal area division method:

$$\hat{F} = \frac{1}{2N}\sum_{k=1}^{N} u_k \quad \text{Equation 12}$$

Errors according to the three methods described above can be compared with each other by estimating relative errors e with respect to the true value of the respiratory gas flow through equation 13.

$$e = \frac{\hat{F} - F}{F} \times 100\% \quad \text{Equation 13}$$

Figure 6A:
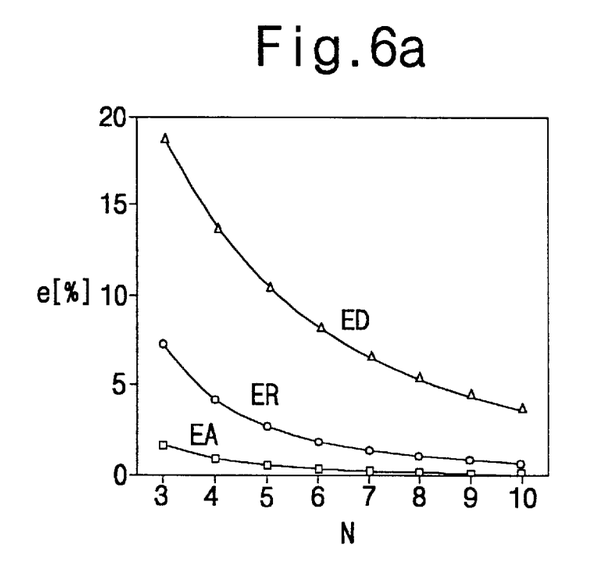
FIG. 6a is a graph showing a change of relative errors according to the number N of the sampling locations.

FIG. 6a is a graph showing a change of the relative errors according to the number N of the sampling locations (degree m=5).

As shown in FIG. 6a, in all of the three methods, as the number N increases, that is, as the number of sampling locations increase, the errors are reduced. However, for a specific value of the number N, the equal area division method represents the smallest error. Moreover, in the equal area division method, when N is equal to or larger than four, e is not larger than one percent which is sufficiently small error.

Figure 6B:
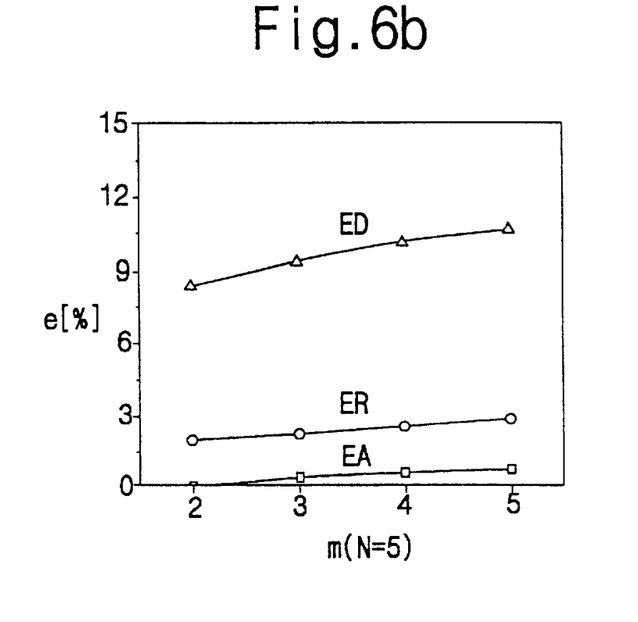
FIG. 6b is a graph showing a change of relative errors according to the increase of the degree.

Further, as shown in FIG. 6b, when N is five, the relative errors increase as the degree m increases. However, it is seen that the equal area division method has the smallest error. Especially in the case of a laminar flow in which m is equal to two, the equal area division method has an error of zero percent, so as to enable a measurement without error to be carried out with only a finite number of samples.

Hereinafter, with reference to FIGS. 3 and 4, described in detail will be the sensing rod 240 employed in the apparatus for measuring respiratory gas flow according to the present invention, which has a plurality of sampling pores whose locations are determined by the equal area division method.

As shown, the sensing rod 240 includes a sensing rod body 241, a pyramidal head 246, and a base 248, which are integrated with each other.

In the present embodiment, N is put as four, that is, eight sampling holes in total are formed through upper and lower portions of the sensing rod body 241 of the sensing rod 240.

The cylindrical tube body 220 has a radius of 12.5 mm which is equal to a standard value of a usual disposable respiratory tube used in the examination of vital capacity. As a result, the locations of the sampling pores are estimated to be 4.42, 7.65, 9.88, and 11.69 mm from the center of the cylindrical tube body by equation 9. Each of the sampling pores has theoretically a sectional area of zero but substantially is a circular pore having a finite diameter of 0.5 mm, so that it is difficult to form a sampling pore nearest to the wall of the cylindrical tube body since it is too adjacent to the wall of the cylindrical tube body. Therefore, all of the four pores are shifted 1.44 mm toward the center, so that they are formed at locations of 2.98, 6.21, 8.44, and 10.25 mm from the center of the cylindrical tube body.

Further, the sensing rod 240 has a section of a diamond shape so as to enable streamlines to pass around the sensing rod 240. The air passages 242 are formed inside of the sensing rod body 241 of the sensing rod 240, so that the respiratory gas can transmit the kinetic energy through the air passages 242, so as to physically equalize dynamic pressures caused by the flow velocities sampled by the sampling pores 244. Further, the air passages 242 and the sampling pores 244 are symmetrically formed so as to measure the respiratory gas flow in both directions through the sensing rod 240.

In addition, the pyramidal head 246 of the sensing rod 240 has a pyramid shape. In this case, the lower surface of the pyramidal head 246 has an area larger than a sectional area of the sensing rod body 241, so as to form an upper jaw 246a which is engaged with an upper portion of the cylindrical tube body 220 to maintain the sensing rod 240 assembled with the respiratory tube assembly 200.

Further, the base 248 of the sensing rod 240 is formed under the sensing rod body 241 and has a shape of a tail of an arrow, so as to enable the two directions of the gas flow to be distinguished. The base 248 has a sectional area larger than the sectional area of the sensing rod body 241, so that the base 248 can be easily assembled with the differential pressure sensor 120 in the measurement module 100. Since the sectional area of the base 248 is larger than the sectional area of the sensing rod body 241, a lower jaw 248a is formed between the sensing rod body 241 and the base 248. The lower jaw 248a and the upper jaw 246a enable the sensing rod 240 to be stably fixed in the respiratory tube assembly 200.

Meanwhile, it is preferred that the sensing rod 240 is inserted through an inserted body 190 fitted at an upper portion of the measurement module 100. The inserted body 190 has two air holes 190a and 190b extending vertically through the inserted body 190. The air holes 190a and 190b are connected with the air passages 242 formed in the sensing rod 240.

As described above, the respiratory tube assembly 200 having the sampling pores whose locations are determined by the equal area division method can largely reduce errors in a measurement of the respiratory gas flow.

Further, the respiratory tube assembly 200 may be made of plastic through an injection molding, so that the sensing rods can be easily mass-produced through the injection molding, thereby reducing their manufacturing cost.

As described above, in an apparatus for measuring respiratory gas flow according to the present invention, a sensing rod having a plurality of sampling pores whose locations are determined by the equal area division method is detachably assembled with a disposable respiratory tube assembly, which is a mouthpiece. Therefore, only if the disposable respiratory tube assembly is replaced, the apparatus for measuring respiratory gas flow according to the present invention may be used nearly permanently without other reasons such as a damage to the measurement module, etc. Also, the sampling pores whose locations are determined by the equal area division method improve the accuracy in the measurement of the respiratory gas flow.

In conclusion, the present invention provides an apparatus for measuring respiratory gas flow, which not only improves the accuracy in the measurement of the respiratory gas flow but also reduces the manufacturing cost of the apparatus.

Although a preferred embodiment of the present invention has been described for illustrative purposes, those skilled in the art will appreciate that various modifications, additions and substitutions are possible, without departing from the scope and spirit of the invention as disclosed in the accompanying claims.

What is claimed is:

1. An apparatus for measuring respiratory gas flow, the apparatus comprising:
   a measurement module containing a differential pressure sensor; and
   a respiratory tube assembly detachably assembled with the measurement module, wherein the respiratory tube comprises:
     a cylindrical tube body having two rod holes formed through a cylindrical wall of the cylindrical tube body wherein the rod holes are disposed at opposite ends of a diameter of the cylindrical tube body, and each of the rod holes has a shape of a diamond;
     a sensing rod having a diamond-shaped cross-section detachably inserted through the rod holes, the sensing rod having a plurality of sampling pores formed through both sides of said rod, and two air passages formed vertically through the sensing rod, the air passages being separated from each other, the sampling pores being formed through both sides of the sensing rod, a first half of the sampling pores facing toward an entrance of the respiratory tube assembly and communicating with a first one of the air passages, a second half of the sampling pores facing toward an exit of the respiratory tube assembly and communicating with a second one of the air passages, the first half of the sampling pores being located symmetrically to the second half of the sampling pores,
   wherein locations of the sampling pores are determined by an equal area division method in which a semicircular section of the cylindrical tube body is divided into a plurality of annuluses with equal areas and the sampling pores are formed at the positions also equally dividing the annuluses to which the sampling locations belong,
   wherein the sensing rod comprises a sensing rod body, a pyramidal head formed on the sensing rod body, and a base formed under the sensing rod body, which are integrated with each other, the pyramidal head having a lower surface whose area is larger than a sectional area of the sensing rod body, so as to form an upper jaw between the sensing rod body and the pyramidal head, the base having a sectional area larger than the sectional area of the sensing rod body, so as to form a lower jaw between the base and the sensing rod body, the upper jaw and the lower jaw enabling the sensing rod to be stably fixed in the respiratory tube assembly, wherein the locations of the sampling pores are determined by a first expression, $$r_k = \sqrt{\frac{2k-1}{2N}}$$

in which k=1, 2, ..., and N, and an estimated value of the respiratory gas flow is obtained by a second expression, $$\hat{F} = \frac{1}{2N}\sum_{k=1}^{N} u_k$$

in which k=1, 2, ..., and N, $u_k$ represents velocities of the respiratory gas, and $\hat{F}$ is the estimated value of the respiratory gas flow.

2. An apparatus for measuring respiratory gas flow as claimed in claim 1, wherein the measurement module further comprises a thermistor, and the respiratory tube assembly has a thermistor hole formed through the cylindrical tube body, the thermistor extending upward from the measurement module and being fitted in the thermistor hole.

3. An apparatus for measuring respiratory gas flow as claimed in claim 1, wherein the sensing rod has a shape of a number "1".

4. An apparatus for measuring respiratory gas flow as claimed in claim 1, wherein the respiratory tube assembly comprises a screen cap which has a net shape and is capped on the entrance of the cylindrical tube body, so as to stabilize streamline of the respiratory gas flow.

* * * * *